United States Patent
Walker

(10) Patent No.: US 6,843,392 B1
(45) Date of Patent: Jan. 18, 2005

(54) VALVE WITH A VALVE STEM WIPER

(75) Inventor: Richard Ian Walker, Ware (GB)

(73) Assignee: Smith Kline Beecham, Philadelphia, PA (US)

( * ) Notice: Subject to any disclaimer, the term of this patent is extended or adjusted under 35 U.S.C. 154(b) by 129 days.

(21) Appl. No.: 10/031,940

(22) PCT Filed: Jul. 4, 2000

(86) PCT No.: PCT/EP00/06226

§ 371 (c)(1),
(2), (4) Date: Jan. 22, 2002

(87) PCT Pub. No.: WO01/10742

PCT Pub. Date: Feb. 15, 2001

(30) Foreign Application Priority Data

Aug. 7, 1999 (GB) .............................. 9918627

(51) Int. Cl.[7] .............................................. B65D 83/00
(52) U.S. Cl. ..................... 222/402.1; 277/568; 277/945
(58) Field of Search .......................... 222/402.1, 321.9; 277/945, 562, 568

(56) References Cited

U.S. PATENT DOCUMENTS

| 2,886,217 A | 5/1959 | Thiel |
| 3,158,179 A | 11/1964 | Lehman et al. |
| 3,180,374 A | 4/1965 | Muller |
| 3,869,072 A | 3/1975 | Eyerdam et al. |
| 3,870,203 A | 3/1975 | Frakenberg |
| 3,900,139 A | 8/1975 | Myers et al. |
| 3,958,727 A | 5/1976 | Steiman |
| 4,013,197 A | 3/1977 | Ewald |
| 4,034,899 A | 7/1977 | Meshberg |
| 4,133,461 A | 1/1979 | Vercelot |
| 4,223,808 A | 9/1980 | Williams et al. |
| 4,349,135 A | 9/1982 | Busselet |
| 4,886,241 A | 12/1989 | Davis et al. |
| 4,893,393 A | 1/1990 | Marshall |
| 4,919,312 A * | 4/1990 | Beard et al. .............. 222/402.2 |
| 5,027,986 A * | 7/1991 | Heinzel et al. ......... 222/402.24 |
| 5,037,012 A | 8/1991 | Langford |
| 5,037,013 A | 8/1991 | Howlett |
| 5,056,757 A | 10/1991 | Wood |
| 5,284,182 A | 2/1994 | McLennan |
| 5,290,539 A | 3/1994 | Marecki |
| 5,632,421 A | 5/1997 | Colombo |
| 5,752,631 A | 5/1998 | Yabuno et al. |
| 5,771,931 A | 6/1998 | Watson |
| 5,772,085 A * | 6/1998 | Bryant et al. ............. 222/402.2 |
| 5,836,299 A | 11/1998 | Kwon |
| 6,170,717 B1 | 1/2001 | Di Diovanni et al. |
| 6,315,173 B1 | 11/2001 | Di Giovanni et al. |

FOREIGN PATENT DOCUMENTS

| EP | 260067 | 3/1988 |
| EP | 616953 | 9/1994 |
| EP | 642992 | 3/1995 |
| EP | 796804 | 9/1997 |
| EP | 796805 | 9/1997 |
| EP | 0 870 699 A | 10/1998 |

(List continued on next page.)

OTHER PUBLICATIONS

U.S. patent application Ser. No. 09/937,232–Filed Feb. 23, 2000, Anderson et al.

Primary Examiner—Philippe Derakshani
(74) Attorney, Agent, or Firm—J. Michael Strickland

(57) ABSTRACT

A valve for use with an aerosol container including a valve body, a valve stem having a dispensing passage, and a sealing ring contacting the valve stem. The sealing ring includes a sealing portion. The valve stem is slidably moveable relative to the sealing ring from a valve-closed position to a valve-open position. The interior of the valve body is in communication with the dispensing passage when the valve stem is in the valve-open position. The sealing ring also includes a wiper component to wipe the valve stem. The valve is preferably a metering valve.

57 Claims, 2 Drawing Sheets

FOREIGN PATENT DOCUMENTS

| | | |
|---|---|---|
| EP | 0870699 A | 10/1998 |
| FR | 1437899 A | 7/1966 |
| GB | 1 397 930 | 6/1975 |
| GB | 1 428 182 | 3/1976 |
| GB | 1 429 766 | 3/1976 |
| GB | 2086845 | 5/1982 |
| GB | 2 093 955 A | 9/1982 |
| GB | 2195986 | 4/1988 |
| GB | 2198117 | 6/1988 |
| GB | 2307224 | 5/1997 |
| GB | 2307278 | 5/1997 |
| GB | 2324121 | 10/1998 |
| GB | 2326156 | 12/1998 |
| GB | 2 326 156 A | 12/1998 |
| WO | 92/11190 | 7/1992 |
| WO | 93/14005 | 7/1993 |
| WO | 93/22221 | 11/1993 |
| WO | 94/01347 | 1/1994 |
| WO | 94/29192 | 12/1994 |
| WO | 95/02651 | 1/1995 |
| WO | 95/03984 | 2/1995 |
| WO | 95/03985 | 2/1995 |
| WO | 95/12533 | 5/1995 |
| WO | 9628367 | 9/1996 |
| WO | 98/29321 | 7/1998 |
| WO | 98/48203 | 10/1998 |
| WO | 98/07010 | 12/1998 |
| WO | 99/00315 A | 1/1999 |
| WO | 99 06303 A | 2/1999 |
| WO | 99/36334 | 7/1999 |
| WO | 00/56632 | 9/2000 |

* cited by examiner

VALVE WITH A VALVE STEM WIPER

This application is filed pursuant to 35 U.S.C. § 371 as a United States National Phase Application of International Application No. PCT/EP00/06226 filed Jul. 4, 2000, which claims priority from GB 9918627.2 filed Aug. 7, 1999.

FIELD OF INVENTION

This invention relates to a valve for an aerosol container with the aid of which a quantity of the contents thereof can be dispensed. The invention has particular application to the dispensing of metered doses of medicaments, though it is applicable to the dispensing of aerosols generally.

BACKGROUND TO THE INVENTION

Containers for aerosol formulations commonly comprise a vial body coupled to a valve. The valve comprises a valve stem through which the formulation is dispensed. Generally the valve includes a rubber valve seal intended to allow reciprocal movement of the valve stem while preventing leakage of propellant from the container.

It has been found that in some conventional devices the valve stem tends to drag during the actuation cycle with the result that the user may perceive a 'notchiness' as the valve stem is depressed and released. This may be partly caused by the drug sedimenting or precipitating out of the drug-propellant suspension or solution formulation and depositing on the internal valve components, the presence of drug on the sliding interface creating increased friction during operation.

The Applicants have now found that the above described problem of notchiness may be ameliorated without compromising sealing performance if the valve seal has a wiper component in addition to a sealing portion. The wiper acts on the valve stem to prevent the deposit and accumulation of drug particles and propellant at the point of contact between the sealing portion and the valve stem. The 'notchiness' that can increase with repeated actuations of the aerosol container is therefore reduced.

Any 'notchiness' may be further reduced by shaping the seal so as to reduce the area of contact between the seal and the valve stem. This results in reduced deformation of the seal and a reduction in the friction at the contact point with the valve stem.

SUMMARY OF THE INVENTION

According to one aspect of the present invention there is provided a valve for an aerosol container, the valve comprising a valve body; a valve stem having a dispensing passage, and contacting said valve stem, a sealing ring including a sealing portion; the valve stem being slidably movable relative to the sealing ring from a valve-closed position to a valve-open position in which the interior of the valve body is in communication with the dispensing passage, wherein the sealing ring further includes a wiper to wipe the valve stem.

Preferably the valve body has a metering chamber, a sampling chamber and therebetween is provided a second sealing ring, including a sealing portion, within which the stem is slidably movable, the valve stem having a transfer passage such that in the valve-closed position the dispensing passage is isolated from the metering chamber and the metering chamber is in communication with the sampling chamber via said transfer passage, and in the valve-open position the dispensing passage is in communication with the metering chamber and the transfer passage is isolated from the metering chamber, wherein the second sealing ring further includes a wiper to wipe the valve stem.

The wiper is typically longer and thinner than the sealing portion of the sealing ring and second sealing ring. The wiper acts to wipe drug deposits away from the stem and does not itself have a primary sealing role.

Preferably the wiper is an integral part of the sealing ring or second sealing ring.

Preferably the wiper of the sealing ring or second sealing ring is in curved contact with the valve stem.

Preferably there is an enclosed space between the wiper, the sealing portion and the seal receiving part of the valve stem.

In one aspect the stem-receiving part of the sealing portion and wiper have square-cut edges.

In another aspect the stem-receiving parts of the sealing portion and wiper have rounded edges.

In a further aspect the stem-receiving part of the wiper is pointed.

In one aspect the sealing portion and wiper are spaced by a layer of supporting rigid material.

Preferably said rigid material is selected from the group consisting of polybutylteraphthlate, polyoxymethylene, a metal and nylon. Suitable metals include stainless steel and aluminium.

In one aspect of the invention the stem-receiving part of the sealing portion is lobed.

Optionally the sealing ring additionally includes a second wiper.

Preferably the sealing ring and second sealing ring are formable by a moulding process. Preferably the moulding process is compression moulding or injection moulding.

Preferably the sealing ring, second sealing ring and wiper are formed from an elastomeric material.

The elastomeric material may either comprise a thermoplastic elastomer (TPE) or a thermoset elastomer which may optionally be cross-linked. The sealing ring and/or second sealing ring may also comprise a thermoplastic elastomer blend or alloy in which an elastomeric material is dispersed in a thermoplastic matrix. The elastomers may optionally additionally contain conventional polymer additives such as processing aids, colorants, tackifiers, lubricants, silica, talc, or processing oils such as mineral oil in suitable amounts.

Suitable thermoset rubbers include butyl rubbers, chlorobutyl rubbers, bromobutyl rubbers, nitrile rubbers, silicone rubbers, flurosilicone rubbers, fluorocarbon rubbers, polysulphide rubbers, polypropylene oxide rubbers, isoprene rubbers, isoprene-isobutene rubbers, isobutylene rubbers or neoprene (polychloroprene) rubbers.

Suitable thermoplastic elastomers comprise a copolymer of about 80 to about 95 mole percent ethylene and a total of about 5 to about 20 mole percent of one or more comonomers selected from the group consisting of 1-butene, 1-hexene, and 1-octene as known in the art. Two or more such copolymers may be blended together to form a thermoplastic polymer blend.

Another suitable class of thermoplastic elastomers are the styrene-ethylene/butylene-styrene block copolymers. These copolymers may additionally comprise a polyolefin (e.g. polypropylene) and a siloxane.

Thermoplastic elastomeric material may also be selected from one or more of the following: polyester rubbers, polyurethane rubbers, ethylene vinyl acetate rubber, styrene butadiene rubber, copolyether ester TPE, olefinic TPE, polyester amide TPE and polyether amide TPE.

Other suitable elastomers include ethylene propylene diene rubber (EPDM). The EPDM may be present on its own or present as part of a thermoplastic elastomer blend or alloy, e.g. in the form of particles substantially uniformly dispersed in a continuous thermoplastic matrix (e.g. polypropylene or polyethylene). Commercially available thermoplastic elastomer blend and alloys include the SANTOPRENE™ elastomers. Other suitable thermoplastic elastomer blends include butyl-polyethylene (e.g. in a ratio ranging between about 2:3 and about 3:2) and butyl-polypropylene.

Preferably the sealing ring and/or second sealing ring is not movable relative to the valve body. More preferably the sealing ring and/or second sealing ring is held within a cavity in the valve body.

Preferably the stem comprises lubricant material. Suitably the valve stem comprises up to 30%, preferably from 5 to 20% lubricant material.

Preferably the sealing ring and/or second sealing ring comprises lubricant material. Suitably, the sealing ring and/or second sealing ring comprise up to 30%, preferably from 5 to 20% lubricant material.

According to another aspect of the present invention there is provided an aerosol container comprising a valve as described hereinabove.

Preferably the aerosol container comprises a suspension of a medicament in a propellant. Preferably the propellant is liquefied HFA134a or HFA-227.

Preferably the medicament is selected from the group consisting of albuterol, salmeterol, fluticasone propionate, beclomethasone dipropionate, salts or solvates thereof and any combination thereof.

A particularly preferred combination comprises salmeterol xinafoate and fluticasone propionate.

BRIEF DESCRIPTION OF THE DRAWINGS

The invention will now be described further with reference to the accompanying drawings in which.

DETAILED DESCRIPTION OF THE DRAWINGS

Figure 1:
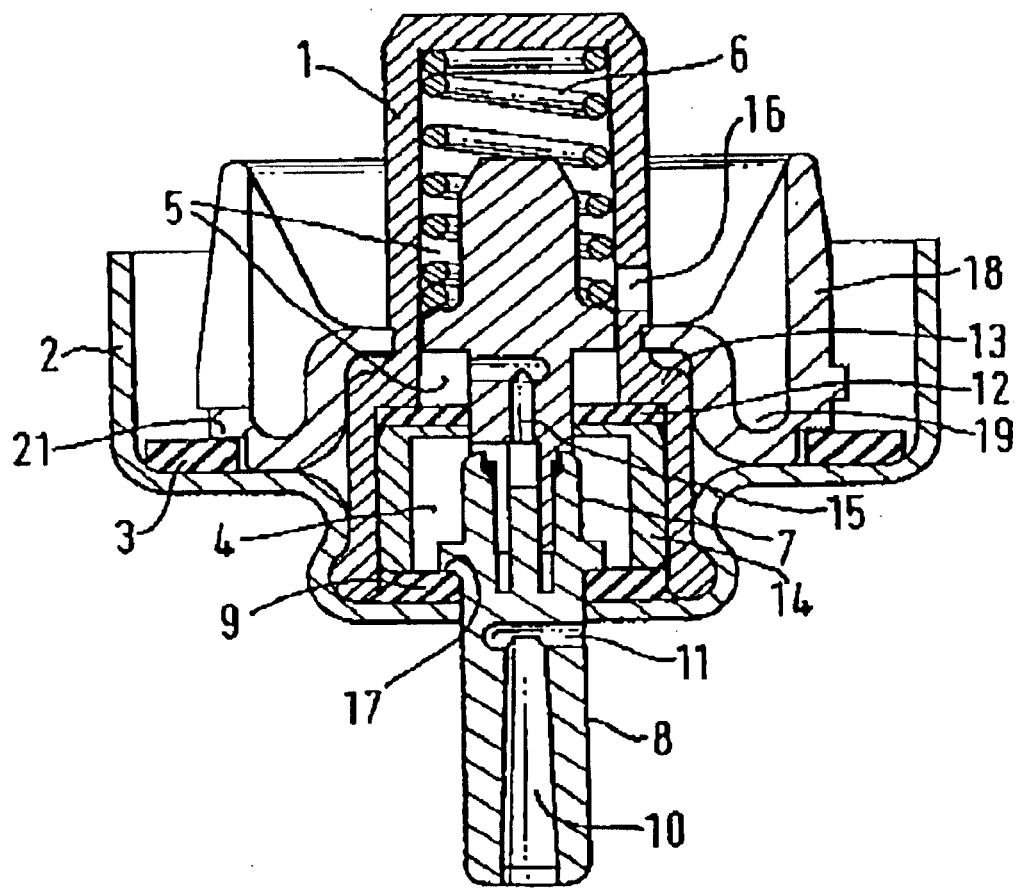
FIG. 1 is a section through a prior art metering valve.

A prior art metering valve is shown in FIG. 1 and comprises a valve body 1 sealed in a ferrule 2 by means of crimping, the ferrule itself being set on the neck of a container (not shown) with interposition of a gasket 3 in a well-known manner. The container is loadable with a suspension of medicament, such as salmeterol xinafoate in liquid propellant HFA134a.

The valve body 1 is formed at its lower part with a metering chamber 4, and its upper part with a sampling chamber 5 which also acts as a housing for a return spring 6. The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2. The stem part 8 is formed with an inner axial or longitudinal canal 10 opening at the outer end of the stem and in communication with a radial passage 11.

The upper portion of stem 7 has a diameter such that it can pass slidably through an opening in an upper stem seal 12 and will engage the periphery of that opening sufficiently to provide a seal. Upper stem seal 12 is held in position against a step 13 formed in the valve body 1 between the said lower and upper parts by a sleeve 14 which defines the metering chamber 4 between lower stem seal 9 and upper stem seal 12. The valve stem 7 has a passage 15 which, when the stem is in the inoperative position shown, provides a communication between the metering chamber 4 and sampling chamber 5, which itself communicates with the interior of the container via orifice 16 formed in the side of the valve body 1.

Valve stem 7 is biased downwardly to the inoperative position by return spring 6 and is provided with a shoulder 17, which abuts, against lower stem seal 9. In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

A ring 18 having a "U" shaped cross section extending in a radial direction is disposed around the valve body below orifice 16 so as to form a trough 19 around the valve body. As seen in FIG. 1 the ring Is formed as a separate component having an inner annular contacting rim of a diameter suitable to provide a friction fit over the upper part of valve body 1, the ring seating against step 13 below the orifice 16. However, the ring 18 may alternatively be formed as an integrally moulded part of valve body 1.

To use the device the container is first shaken to homogenise the suspension within the container. The user then depresses the valve stem 7 against the force of the spring 6. When the valve stem is depressed both ends of the passage 15 come to lie on the side of upper stem seal 12 remote from the metering chamber 4. Thus a dose is metered within the metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and sampling chamber 5. Accordingly, at this stage liquid passes under pressure from the container through orifice 16, through the passage 15 and thence into the metering chamber 4 to fill it.

FIG. 1 illustrates a prior art valve with square cut valve seals while the current invention describes the use of a wiper seal to wipe the valve stem and consequently reduce the 'notchiness' during actuation of the inhaler device. The wiper and sealing portion of the sealing ring replace the square cut seals (9 and 12) shown in FIG. 1. The detail of the wiper and sealing portion of the sealing ring according to the invention are described below and illustrated in FIGS. 2a and 2b.

Figure 2A:
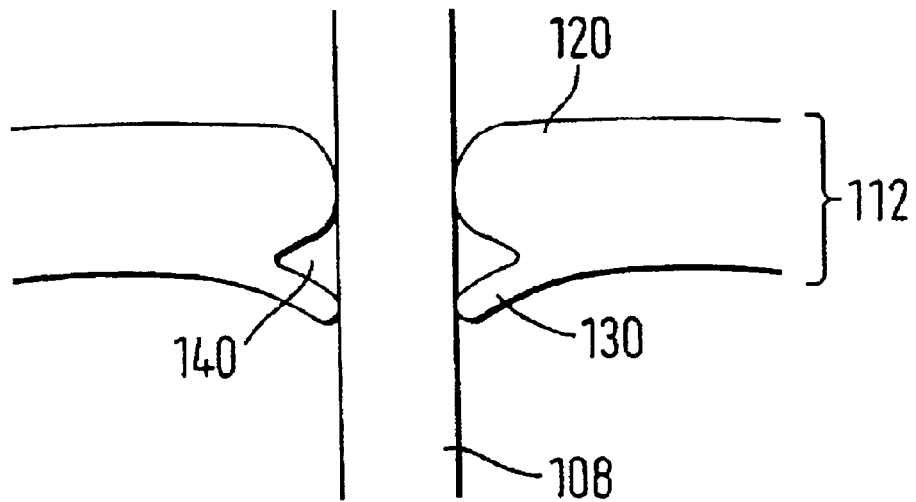
FIGS. 2a and 2b are close up sectional views of a seal-stem contact point in a valve according to the invention, showing two different arrangements and shapes of the sealing portion and wiper of the sealing ring or second sealing ring.

FIG. 2a shows upright valve stem 108, which has a circular cross-section. A sealing ring 112 sealingly contacts the valve stem 108. The sealing ring 112 is comprised, at the stem receiving part, of a sealing portion 120 and a wiper 130.

Figure 2B:
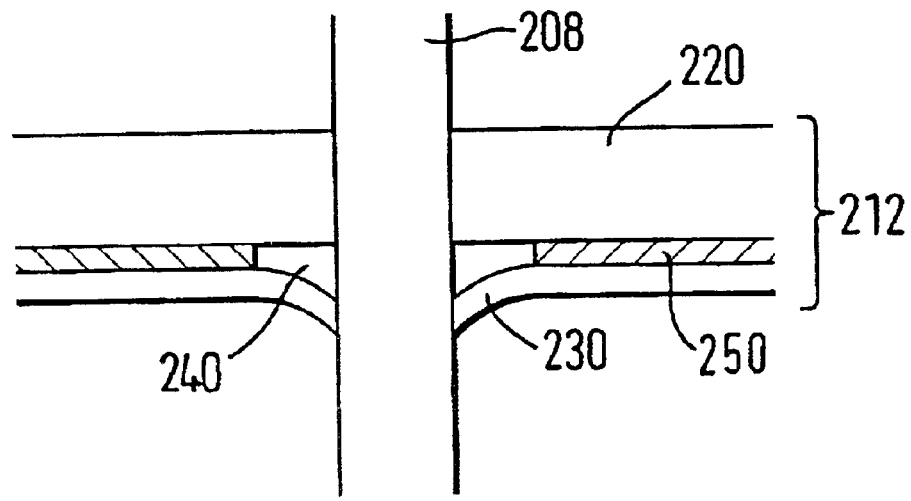

The wiper 130 is in curved contact with the valve stem 108 and is separated from the sealing portion 120 by an enclosed space 140. The wiper 130 wipes the valve stem 108 so that any particles are wiped away from the sealing portion 120 of the sealing ring 112. The wiper does not have a sealing function. The wiper 130 is long and thin in comparison to the sealing portion 120 and the length of the wiper 130 may be varied for optimum performance FIG. 2b shows upright valve stem 208, which has a circular cross section. A sealing ring 212 sealingly contacts the valve stem 208. The sealing ring 212 is comprised, at the stem-receiving part, of a sealing portion 220 and a wiper 230. The wiper 230 and sealing portion 220 are separated at the stem receiving part by a small enclosed space 240 and are supported by a layer of rigid material The wiper 230 wipes the valve stem 208 so that any particles are wiped away from the sealing portion 220 of the sealing ring 212. The wiper 230 is long and thin in comparison to the sealing portion 220 and the length of the wiper 230 may be varied for optimum performance. The supporting layer of rigid material 250 supports the sealing portion 220 and wiper 230 and reduces the deformation of the sealing portion 220 during movement of the valve stem 208. The supporting layer thereby reduces the surface contact area between the sealing portion 220 and the valve stem 208 and consequently further reduces the problem of 'notchiness'.

The aerosol container and valve of the invention is suitable for dispensing medicament, particularly for the treatment of respiratory disorders. Medicaments which may be administered in the aerosol formulations include any drug useful in inhalation therapy. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracydines and pentamidine; antihistamines, e.g. methapyrilene; ant-inflammatories, e.g. beclomethasone, flunisolide, budesonide, tipredane, triamcinolone acetonide, fluticasone or mometasone; antitussives, e.g. noscapine; bronchodilators, e.g. ephedrine, epinephrine, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, 4-hydroxy-7-[2-[[2-[[3-(2-phenylethoxy)propyl]sulfonyl]ethyl]amino]ethyl-2(3H)-benzothiazol; orciprenaline, or (−)-4-amino-3,4-dichloro-α-[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament and/or to minimize the solubility of the medicament in the propellant. It will further be clear to a person skilled in the art that where appropriate, the medicaments may be used in the form of a pure isomer, for example, R-salbutamol or RR formoterol.

Particularly preferred medicaments for administration using aerosol formulations in accordance with the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or the sulphate salt), salmeterol (e.g. as the xinafoate salt), formoterol (e.g. as the fumarate salt), terbutaline (e.g. as the sulphate salt), reproterol (e.g. as the hydrochloride salt), a beclomethasone ester (e.g. the dipropionate), a fluticasone ester (e.g. the propionate). Salmeterol, especially salmeterol xinafoate, salbutamol, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Aerosol compositions containing two active ingredients are known for the treatment of respiratory disorders such as asthma, for example, formoterol and budesonide, salmeterol (e.g. as the xinafoate salt) and fluticasone (e.g. as the propionate ester), salbutamol and beclomethasone (as the dipropionate ester) are preferred.

The term 'lubricant' herein means any material that reduces friction between the valve stem and seal or reduces the tendency of medicament to adhere to any parts of the metering valve which contact the medicament suspension. Suitable lubricants include fluoropolymers such as polytetrafluoroethylene (PTFE), fluoroethylene propylene (FEP), polyfluoro-cyclohexane, polyfluoro-hexane, trifluoroethylene, vinylidene fluoride and vinyl fluoride. Other suitable inorganic coatings which may be used to reduce adherence or which enhance the barrier properties to HFA134a, moisture, or drug absorption, include silicone oil or siloxanes such as dimethyl siloxane. Any movable parts may also have coatings applied thereto, which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations, and improvements thereto.

The application of which this description and claims form part may be used as a basis for priority in respect of any subsequent application. The claims of such a subsequent application may be directed to any feature or combination of features described therein. They may take the form of product, method or use claims and may include, by way of example and without limitation, one or more of the following claims:

What is claimed is:

1. A valve comprising:
    a valve body defining a metering chamber in communication with a dispensing passage; and,
    a valve stem having the dispensing passage and transfer passage, the valve stem contacting and slidably movable with respect to
    a first sealing ring including a first sealing portion and a first wiper portion, wherein a stem-receiving part of the first sealing portion contacts a first of the valve stem, wherein a stem-receiving part of the first wiper portion contacts a second surface of the valve stem, and wherein there is an enclosed space between the first sealing portion, the first wiper portion, and a valve stem surface between the first surface of the valve stem and the second surface of the valve stem.

2. The valve according to claim 1, further including:
    a sampling chamber; and,
    a second sealing ring including a second sealing portion, wherein, in a valve-closed position, the dispensing passage is isolated from the metering chamber and the metering chamber is in communication with the sampling chamber via said transfer passage, wherein, in the valve-open position, the dispensing passage is in communication with the metering chamber and the transfer passage is isolated from the metering chamber; and, wherein the second sealing ring further includes a second wiper position adapted to wipe the valve stem.

3. The valve according to claim 1, wherein the first wiper portion is integral to the first sealing ring.

4. The valve according to claim 1, wherein the first wiper portion is in curved contact with the valve stem.

5. The valve according to claim 1, wherein the first sealing portion includes a square cut edge.

6. The valve according to claim 1 wherein the first sealing portion includes a rounded edge.

7. The valve according to claim 1, wherein the first wiper portion includes a tapered portion.

8. The valve according to claim 1, further including a first layer of rigid material supporting the first wiper and sealing portion.

9. The valve according to claim 8 wherein the layer is constructed from a material selected from the group consisting of a polybutylteraphthlate, polyoxymethylene, metal and nylon.

10. The valve according to claim 1, wherein the first sealing portion includes a lobed portion.

11. The valve according to claim 1, wherein the first sealing ring is constructed by moulding.

12. The valve according to claim 11, wherein the first sealing ring is made by compression moulding or injection moulding.

13. The valve according to claim 1, wherein the first sealing ring is formed from an elastomeric material.

14. The valve according to claim 13 wherein the elastomeric material is selected from the group consisting of:
a copolymer of about 80 to about 95 mole % ethylene and about 5 to about 20 mole % of one or more of 1-butene, 1-hexene and 1-octene;
a styrene-ethylene/butylene-styrene block copolymer;
an ethylene propylene diene rubber;
a styrene-ethylene/butylene-styrene dispersed in a polypropylene or polyethylene matrix;
a butyl polyethylene;
a butyl-polypropylene; and
mixtures thereof.

15. The valve according to claim 1, wherein the first sealing ring is fixed relative to the valve body.

16. The valve according to claim 15, wherein the first sealing ring is fixed within a cavity in the valve body.

17. A drug product comprising:
an aerosol container in communication with
a valve according to claim 1.

18. The drug product of claim 17, further comprising a suspension of medicament in a propellant contained within the aerosol container.

19. The drug product according to claim 18, wherein the propellant is liquefied HFA134a or HFA-227 or mixtures thereof.

20. The drug product according to claim 18, where the medicament is selected from the group consisting of albuterol, salmeterol, fluticasone, beclomethasone, salt, esters or solvates thereof, and combinations thereof.

21. The drug product according to claim 20 wherein the medicament comprises salmeterol xinafoate and fluticasone propionate.

22. The valve according to claim 1, wherein the first sealing ring includes a second wiper portion.

23. A valve comprising:
a valve body defining a metering chamber in communication with a dispensing passage; and,
a valve stem having the dispensing pass go and a transfer passage, the valve stem contacting and slidably movable with respect to
a sealing ring including a sealing portion and a wiper portion, wherein the wiper portion is in curved contact with the valve stem.

24. The valve according to claim 23, wherein the wiper portion is integral to the sealing ring.

25. The valve according to claim 23, wherein a stem-receiving part of the sealing portion that contacts the valve stem has a rounded edge.

26. The valve according to claim 23, wherein a layer of rigid material is positioned between the sealing portion and the wiper portion.

27. The valve according to claim 26, wherein the layer is constructed from a material selected from the group consisting of a polybutylteraphthlate, polyoxymethylene, metal and nylon.

28. The valve according to claim 23, wherein the sealing ring includes a first wiper portion and a second wiper portion.

29. The valve according to claim 23, wherein the sealing ring comprises an elastomeric material.

30. A drug product comprising:
an aerosol container in communication with
a valve according to claim 23.

31. The drug product according to claim 30, further comprising a suspension of medicament in a propellant contained within the aerosol container.

32. The drug product according to claim 31, wherein the propellant is liquified HFA134a or HPA-227 or mixtures thereof.

33. The drug product according to claim 31, wherein the medicament is selected from the group consisting of albuterol, salmeterol fluticasone, beclomethasone, salts, esters or solvates thereof, and combinations thereof.

34. A valve comprising:
a valve body defining a metering chamber in communication with a dispensing passage; and,
a valve stem having the dispensing passage and a transfer passage, the valve stem contacting and slidably movable with respect to
a sealing ring including a sealing portion, a wiper portion, and a layer of supporting rigid material positioned between the sealing portion and the wiper portion.

35. The valve according to claim 34, wherein the layer is constructed from a material selected from the group consisting of a polybutylteraphthlate, polyoxymethylene, metal and nylon.

36. The valve according to claim 34, wherein a stem-receiving part of the sealing portion contacts a first surface of the valve stem, a stem-receiving part of the wiper portion contacts a second surface of the valve stem, and there is an enclosed space between the sealing portion, the wiper portion, and a valve stem surface between the first surface of the valve stem and the second surface of the valve stem, and wherein the wiper portion is in curved contact with the valve stem.

37. The valve according to claim 34, wherein the wiper portion is integral to the sealing ring.

38. The valve according to claim 34, wherein a stem-receiving part of the sealing portion contacts the valve stem and has a rounded edge.

39. The valve according to claim 34, wherein the sealing ring includes a first wiper portion and a second wiper portion.

40. The valve according to claim 34, wherein the sealing ring comprises an elastomeric material.

41. A drug product comprising:
an aerosol container in communication with
a valve according to claim 34.

42. The drug product according to claim 41, further comprising a suspension of medicament in a propellant contained within the aerosol container.

43. The drug product according to claim 42, wherein the propellant is liquified HFA134a or HFA-227 or mixtures thereof.

44. The drug product according to claim 42, wherein the medicament is selected from the group consisting of albuterol, salmeterol, fluticasone, beclomethasone, salts, esters or solvates thereof, and combinations thereof.

45. A valve comprising:
a valve body defining a metering chamber in communication with a dispensing passage;
a sampling chamber;
a valve stem having the dispensing passage and a transfer passage, the valve stem contacting and slidably movable with respect to
a first sealing ring including a first sealing portion; and
a second sealing ring including a second sealing portion;
wherein, in a valve-closed position, the dispensing passage is isolated from the metering chamber and the metering chamber is in communication with the sampling chamber via said transfer passage;
wherein, in the valve-open position, the dispensing passage is in communication with the metering chamber and the transfer passage is isolated from the metering chamber;
wherein the first sealing ring further includes a first wiper portion adapted to wipe the valve stem;
wherein the second sealing ring further includes a second wiper portion adapted to wipe the valve stem; and
wherein the first and/or second sealing ring is constructed by a moulding process.

46. A valve comprising:
a valve body; and
a valve stem having a dispensing passage, and, said valve stem, a sealing ring including a sealing portion; the valve stem being slidably movable relative to the sealing ring from a valve-closed position to a valve-open position in which the interior of the valve body is in communication with the dispensing passage, wherein the sealing ring further includes a wiper portion configured to wipe the valve stem on sliding movement of the valve stem relative to the sealing ring, wherein the sealing portion presents a sealing surface in sealing engagement with the valve stem, wherein the wiper portion presents a wiper surface in wiping engagement with the valve stem, and wherein the sealing ring further has a void portion which is juxtaposed to the valve stem and located between the sealing and wiper surfaces for spatial separation of the sealing and wiper surfaces.

47. The valve according to claim 46, wherein the wiper portion is an integral part of the sealing ring.

48. The valve according to claim 46, wherein the wiper portion is in curved contact with the valve stem.

49. The valve according to claim 46, wherein the sealing surface and the wiping surface have rounded edges.

50. The valve according to claim 46, wherein the seal and wiper are spaced apart by a layer of supporting rigid material.

51. The valve according to claim 46, wherein the rigid material is selected from the group consisting of polybutylteraphthlate, polyoxymethylene, a metal and nylon.

52. The valve according to claim 46, wherein the sealing ring comprises a first wiper and a second wiper.

53. The valve according to claim 46, wherein the sealing ring comprises an elastomer material.

54. A drug product comprising:
an aerosol container in communication with
a valve according to claim 46.

55. The drug product according to claim 54, further comprising a suspension of medicament in a propellant contained within the aerosol container.

56. The drug product according to claim 55, wherein the propellant is liquefied HFA134a or HFA-277 or mixtures thereof.

57. The drug product according to claim 55, wherein the medicament is selected from the group consisting of albuterol, salmeterol, fluticasone, beclomethasone, salts, esters or solvates thereof, and combinations thereof.

* * * * *

UNITED STATES PATENT AND TRADEMARK OFFICE
CERTIFICATE OF CORRECTION

PATENT NO. : 6,843,392 B1
DATED : January 18, 2005
INVENTOR(S) : Richard Ian Walker It is certified that error appears in the above-identified patent and that said Letters Patent is hereby corrected as shown below:

Column 6,
Line 55, should read -- first sealing portion contacts a first surface of the valve stem, --.

Column 7,
Line 8, should read -- wiper portion adapted to wipe the valve stem. --.
Line 61, should read -- The drug product according to claim 18, wherein the --.
Line 63, should read -- albuterol, salmeterol, fluticasone, beclomethasone, salts, --.

Column 8,
Line 6, should read -- a valve stem having the dispensing passage and a transfer --.
Line 35, should read -- propellant is liquefied HFA134a or HFA-227 or mixtures --.
Line 39, should read -- albuterol, salmeterol, fluticasone, beclomethasone, salts, --.

Column 9,
Line 47, should read -- a valve stem having a dispensing passage, and, contacting said valve --.

Column 10,
Line 25, should read -- The valve according to claim 50, wherein the rigid --.
Line 32, should read -- ring comprises an elastomeric material. --.

Signed and Sealed this

Eleventh Day of April, 2006

JON W. DUDAS
*Director of the United States Patent and Trademark Office*